United States Patent [19]

Hiltebrandt

[11] Patent Number: 4,682,585
[45] Date of Patent: Jul. 28, 1987

[54] OPTICAL SYSTEM FOR AN ENDOSCOPE

[75] Inventor: Siegfried Hiltebrandt, Knittlingen, Fed. Rep. of Germany

[73] Assignee: Richard Wolf GmbH, Fed. Rep. of Germany

[21] Appl. No.: 826,187

[22] Filed: Feb. 5, 1986

[30] Foreign Application Priority Data

Feb. 23, 1985 [DE]  Fed. Rep. of Germany ....... 3506464

[51] Int. Cl.⁴ .............................................. A61B 1/00
[52] U.S. Cl. ...................................................... 128/4
[58] Field of Search .................. 128/3, 4, 5, 6, 7, 8, 128/303.15, 305.3, 754

[56] References Cited

U.S. PATENT DOCUMENTS 4,215,678 8/1980 Heine et al. ............................... 128/6
4,589,404 5/1986 Barath et al. ............................ 128/6

Primary Examiner—William H. Grieb
Attorney, Agent, or Firm—Hill, Van Santen, Steadman & Simpson

[57] ABSTRACT

The shaft of an endoscope for passing through a trocar sleeve or a guiding shaft is tapered towards the distal extremity, and this taper is followed proximally by at least one shallowly concave peripheral constriction. The distal objective of the endoscope is thus spaced from the inner walls and distal edges of the trocar sleeve or guiding shaft, so that residues on these inner walls or edges do not contaminate or obscure objective but are instead scraped off by the peripheral constriction.

11 Claims, 3 Drawing Figures

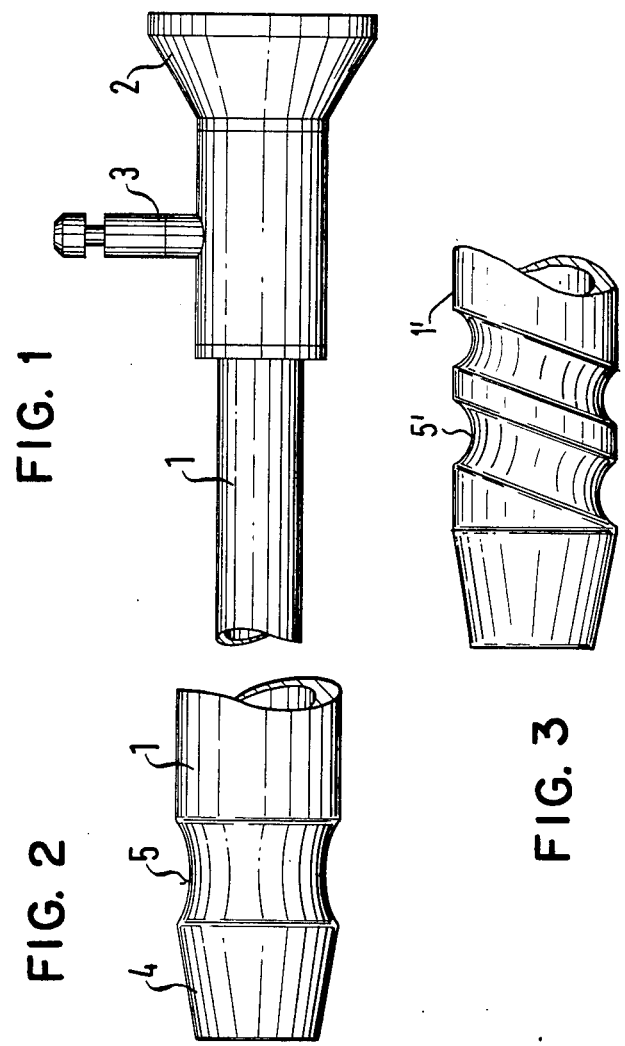

OPTICAL SYSTEM FOR AN ENDOSCOPE

BACKGROUND OF THE INVENTION

The invention relates to an optical system for an endoscope, comprising a shaft receiving the optical elements, which is insertible into a bodily cavity for examination, via a trocar sleeve or a guiding shaft.

DESCRIPTION OF THE PRIOR ART

The case may arise upon passing endoscope optical systems through a trocar sleeve or a guiding shaft that contamination e.g. in the form of secretion or blood residues, is present in the distal extremity of the trocar sleeve or of the guiding shaft, which then obstructs the view of the optical system passed through the trocar sleeve by being deposited on the distal objective of the optical system. The optical system then has to be withdrawn from the sleeve or shaft, cleaned and inserted through the sleeve again, which leads to considerable inconvenience to the patient and delays in endoscopic examination.

SUMMARY OF THE INVENTION

It is an object of the invention so far as possible to preclude soiling of the objective lens of an endoscope optical system which is to be inserted into a bodily cavity via a trocar sleeve or a guiding shaft.

This object is achieved in that in the case of an endoscope optical system of the type referred to in the foregoing, the optical system shaft is tapered conically towards the distal extremity, and in that the taper is followed in the proximal direction by at least one peripheral constriction. The constriction is preferably in the form of a shallow concavity such as an annular or helical peripheral channel.

Thanks to this particular uncomplicated solution, when the distally tapered part of the endoscope optical system shaft is moved past secretion or blood residues or the like present in the distal extremity of the trocar sleeve or guiding shaft, its relatively narrow end portion will be clear of the inner wall and edges of the guiding shaft and of the residues so that soiling of the objective lens of the optical system can no longer occur. Any residue which is initially left behind in the trocar sleeve or guiding shaft upon passing the optical system through, is then scraped off, deposited and entrained at the proximal extremity of the taper and/or of the peripheral constriction. Residue adhering on this extremity of the optical system may be removed in a simple manner after completing the examination.

BRIEF DESCRIPTION OF THE DRAWINGS

FIG. 1 is a partial side view of an endoscope optical system of the present invention with the distal end broken away;

FIG. 2 is an enlarged side view of the distal end of the endoscope of FIG. 1; and FIG. 3 is an enlarged side view of an embodiment of the distal end according to the present invention.

DETAILED DESCRIPTION OF THE PREFERRED EMBODIMENT

The endoscope optical system comprises an optical system shaft 1 receiving the optical elements, having a proximal eyepiece 2 and a light guide connector 3 for light guides extending through the shaft.

The endoscope shaft 1 has a frusto-conical end portion 4 tapering towards the distal extremity, and immediately behind it a peripheral constriction 5 of the shaft 1, which in this case has the form of a shallow concavity of substantially arcuate cross-section, to avoid sharp edges and acute transitions in shape, the concavity is annular, extending circumferentially around the shaft 1.

Instead of the annular constriction 5, it is also possible to provide a shaft 1' with at least one cross-sectionally rounded-off shallow helical groove or screw-thread 5' (FIG. 3). The depth of the constriction should generally be small in relation to the diameter of the shaft. Thanks to the distal frusto-conical end portion 4 and the constriction 5 or 5', the endoscope optical system may be inserted into a bodily cavity through a trocar sleeve or a guiding shaft without contaminations in the distal extremity of the sleeve or the like being liable to reach the objective area of the endoscope optical system, since the tapered distal extremity 4 is always spaced from the inner surface of a trocar sleeve or guiding sleeve, so that this extremity is led past the contaminations in the trocar sleeve and in the area of its distally open extremity. It is only by the extremities of the constriction 5 or 5' that residue particles are freed from the inner surface of the trocar sleeve or from its distally open extremity, and are deposited in the constriction 5 or 5' until they may be cleaned off in a simple manner after completion of the examination.

What is claimed is:

1. An optical system for an endoscope comprising a shaft receiving optical guide elements, said shaft being insertible through guide means into a bodily cavity for examination, said shaft at a distal end having an integral frusto conical portion converging towards the distal extremity, and said shaft having at least one peripheral constriction at a proximal side of the conical portion.

2. An optical system as claimed in claim 1, wherein said constriction is in the form of an annular concavity extending circumferentially around said shaft.

3. An optical system as claimed in claim 1, wherein said constriction is in the form of a helical groove around said shaft.

4. An optical system as claimed in claim 1, wherein said constriction is shallow in relation to the diameter of said shaft.

5. An optical system as claimed in claim 1, wherein said constriction is of substantially arcuate cross-section.

6. An optical system for an endoscope comprising a shaft receiving optical guide elements, which is insertible through guide means into a bodily cavity for examination, said shaft tapers conically towards its distal extremity and on the proximal side of the taper has at least one peripheral constriction having a form of an annular concavity extending circumferentially around said shaft.

7. An optical system according to claim 6, wherein said constriction is shallow in relation to the diameter of said shaft.

8. An optical system according to claim 6, wherein said constriction is of substantially arcuate cross-section.

9. An optical system for an endoscope comprising a shaft receiving optical guide elements, which is insertible through guide means into a bodily cavity for examination, said shaft tapers conically towards its distal extremity and on the proximal side of the taper has at least one peripheral constriction having a form of a helical groove around said shaft.

10. An optical system according to claim 9, wherein said constriction is shallow in relation to the diameter of said shaft.

11. An optical system according to claim 9, wherein said constriction is of substantially arcuate cross-section.

* * * * *